United States Patent [19]

Kortright et al.

[11] Patent Number: 4,870,003

[45] Date of Patent: Sep. 26, 1989

[54] SIMULTANEOUS ENZYME IMMUNOASSAY FOR DETECTING ANTIGEN AND/OR ANTIBODY IN HUMANS

[75] Inventors: Kenneth H. Kortright, Cooper City; David E. Hofheinz, Homestead; David M. Allman; Meryl A. Forman, both of Miami; Song Y. Lee, Plantation; Paulette E. Smariga, North Miami; Candie S. Stoner, Hollywood, all of Fla.

[73] Assignee: Coulter Corporation, Hialeah, Fla.

[21] Appl. No.: 61,979

[22] Filed: Jun. 15, 1987

[51] Int. Cl.$^4$ ............... G01N 33/569; G01N 33/535; G01N 33/545
[52] U.S. Cl. .................................... 435/5; 435/7; 435/810; 436/510; 436/518; 436/531; 436/800; 436/805; 436/808; 436/809; 436/811; 436/825; 436/826
[58] Field of Search ............... 435/5, 7, 810; 436/510, 436/518, 531, 800, 805, 808, 809, 811, 825, 826

[56] References Cited

U.S. PATENT DOCUMENTS

| | | | |
|---|---|---|---|
| 4,172,117 | 10/1979 | Schober | 436/804 |
| 4,661,445 | 4/1987 | Saxinger et al. | 435/5 |
| 4,748,110 | 5/1988 | Paul | 435/5 |

*Primary Examiner*—Christine M. Nucker
*Attorney, Agent, or Firm*—Myron C. Cass

[57] ABSTRACT

A solid-phase immunoassay is provided for determination of members of an immunological pair such as antigen and/or antibody of a single binding pair in human physiological fluid, wherein a single immunoassay enables simultaneous detection of antigen and/or antibody of a single binding pair in a test sample which may have circulating antigen and/or antibody. The immunoassay is characterized by the addition of an amount of antigen or "spike" of the binding pair to the test sample prior to incubation of the test sample in the presence of a solid-phase absorbed antibody of the binding pair. The test sample preferably also is subjected to a lysing reagent prior to the incubation for uniformly dispensing antigens which may be present in the test sample.

14 Claims, No Drawings

SIMULTANEOUS ENZYME IMMUNOASSAY FOR DETECTING ANTIGEN AND/OR ANTIBODY IN HUMANS

The invention provides a single immunoassay for simultaneous detection of antigen and/or antibody of a single binding pair in a human physiological fluid test sample which may have circulating antigen and/or antibody.

This invention in a preferred embodiment provides a unique enzyme immunoassay which can be performed for detecting HIV, HIV fragments, HIV infected cells and/or human antibodies which bind the HIV organism, or HIV antigen-carrying fragments, in a single human plasma or serum sample or cultured cell supernatant. The immunoassay embodying the invention provides a test result of positive antibody, positive antigen or "negative", as the case may be, especially for detection of HIV antigen with greater accuracy or sensitivity, consistency and in a shorter period of time than has been realized heretofore.

BACKGROUND OF THE INVENTION

HTLV III infection, now referred to as HIV infection, commonly results in AIDS (Acquired Immune Deficiency Syndrome). Reported increasing numbers of AIDS patients in the United States has caused the disease to be recognized as approaching epidemic proportions with no known cure or vaccine. The occurrence of AIDS has been increasing primarily in Europe and African countries of the world as the disease is transmitted through sexual activity, drug abuse, contaminated organs in transplantation procedures and by blood transfusions. Other strains of the HIV such as HTLV IV are developing through mutation of this virus.

Separate tests for the presence of HIV antibody or HIV antigen have been developed by investigators, including scientists at the National Institute of Health (NIH). Assays for detecting HIV antibody in plasma and serum have received clinical approval for commercialization. Assays for detecting HIV antigen are known for research use but to our knowledge none has received clinical approval for commercialization. These tests separately and independently analyze the plasma, serum or blood cell culture supernatant of screened individuals for HIV antigen or human anti-HIV antibody content which binds the HIV antigen, see Anti-HIV Testing: Screening and Confirmation Tests, Medical Laboratory Products, April 1987, p. 16–18, for a recent review article comparing several such separate tests.

Human antibody develops in 4 to 6 weeks in 70–80% of the people exposed to HIV through sexual intercourse, blood transfusions, contaminated organs through transplantation or contaminated needles by drug abusers. The remaining 20–30% of exposed individuals who do not develop antibodies against the invading virus for a period of up to six months can remain undetected carriers in society. Therefore, if one is to effectively screen blood and organ donors, individuals, or blood products for containing the spread of AIDS, it is essential that the screening immunoassay be able to detect not only HIV antibody but also the HIV virus itself and/or infected cells carrying the virus.

Heretofore difficulty has been encountered with false-positive results which may occur due to nonspecific antibodies or to antibodies directed against normal cellular antigens in supporting cell cultures used to obtain supernatants containing viral particles in sufficient quantity as is generally necessary to overcome the less than desirable sensitivity of prior tests.

We are not aware of any investigational or clinical immunoassay for simultaneously detecting through analysis of a single moiety of a physiological fluid test specimen both members of a single binding pair such as anti-HIV antibody, the HIV organism or HIV infected blood cells, for instance, such as in a human blood sample. The assay embodying the invention successfully tests for both the virus, virus infected cells and antibodies which bind the HIV organism. The assay can be performed in a single vessel such as a microtiter plate well. Preferably, the patient's test sample comprises human plasma, i.e, whole blood from which all cells have been removed initially, or serum, i.e., plasma from which all clotting factors have been removed. The assay provides a result of "positive" or "negative" as the case may be, by enzyme immunoassay (EIA). The suitability of the use of the assay of this invention to identify AIDS infected patients is significantly greater than has been realized heretofore where an immunoassay tracks only antibodies to HIV in a physiological sample such as peripheral blood. The test result is achieved in approximately four hours.

Lysing of viral concentrates to release viral proteins prior to using electrophoresis to spread viral proteins, i.e., antigens, on polyacrylamide gel is known with respect to a Western, blot technique for confirming the, presence of only anti-HIV antibodies, not antigens, and is thus of no practical utility during that period of time prior to when no antibodies are present even though the patient has been infected with HIV. Similarly, the use of an HIV lysate as a solid phase protein adhered to a solid phase support, such as a microtiter plate formed of polystyrene, is known with respect to an ELISA technique for screening for anti-HIV antibodies, not antigens, during that period after HIV infection when no antibodies are present. However, it has not been recognized that the lysing of HIV in a specimen in contact with an antibody coated solid phase, in the presence of a known amount of HIV antigen prior to incubation of the test sample in the presence of biotinylated antibody comprising a member of a single binding pair, can provide for the relatively rapid, sensitive quantitative measurement of both antibody and antigen in a single test sample.

SUMMARY OF THE INVENTION

An enzyme immunoassay is provided for detecting antigen and/or antibody of a single binding pair in a human physiological fluid test sample such as plasma or serum or cell culture supernatant. In a preferred embodiment of the invention the immunoassay is used to simultaneously test a single sample for HIV antigen and/or antibody wherein the methodology used is that of solid-phase assay, e.g., enzyme-linked immunosorbent assay (ELISA) that uses microtiter plates, microtiter strips, polystyrene beads, or ferrous beads, for example, as support media. In a particularly preferred embodiment the test sample or specimen of predetermined volume, such as 200 microliters (uL), is introduced into a well of a microtiter plate which has been coated with purified anti-HIV antibody prepared from a suitable high titer human, goat, or other mammalian serum or plasma source. For example anti-HIV antibody from goat may be obtained by a conventional injection and bleeding schedule by use of purified HIV which supplies P24, GP120 and GP160 viral proteins or viral glycoproteins. After attainment of sufficient titer of anti-HIV antibody in the goat, anti-HIV antibody is recovered and purified. The sample is subjected to incubation procedures which utilize selected developing reagents.

The assay procedure includes as a significant aspect a step of introducing, into the coated well containing the test sample, a preselected known quantity, for a given volume, of the antigen of the single binding pair being assayed. At the final step of the assay the known quantity of antigen is detectable generally at a preselected quantitative value, such as for example an optical density value for a designated picogram concentration of antigen used which provides not only a "base line" which provides a "negative" test result but more significantly also enables in this single assay sample a quantitative measurement of both antibody positive and/or antigen positive determination. The inactivated or non-infectious viral antigen introduced in this significant aspect of the invention, or provided in a kit for performing the test, is called a "Spike". As will be explained it is the use of the antigen Spike that enables the measurement of both viral antigen and antibody, or absence thereof, in the sample being tested in a single well. For purposes of this disclosure the antigen of the Spike will be understood to not necessarily be limited to being comprised of the antigenic sites, or spikes that protrude from the membrane or envelope of the HIV but will in fact be comprised of a mixture of viral proteins including HIV core protein. The preferred solid phase assay used is the ELISA technique employed to enable visualization of immunological reaction by optical density measurement of visualized reactants. Attention is directed to a series of review articles entitled *Radioimmunoassay and Saturation Analysis*, British Medical Bulletin, Vol. 30, No. 1, Jan. 1974 with respect to visualization of immunological reactions by various methods in respect of various virus and antibody-containing physiological fluids and tissues.

In its broadest sense the dual antibody/antigen test functionality of the method of this invention will be understood to result from the fact that the specific antibody in test sample will bind specifically the viral antigen Spike. If the immunological reaction detection or visualization procedure determines that some or all of the known quantity viral antigen did bind to the specific anti-HIV antibody in the test sample such that less antigen was detected from the Spike, the test result will be construed to be "antibody positive". On the other hand, the antigen in the test sample will add to the known quantity of antigen added by way of the Spike. If the detection procedure shows this additive effect, the test result will be construed to be "antigen positive". However, if the visualization of the immunological reactions of the test result is, for example, an optical density corresponding to the optical density of the predetermined picogram amount of antigen added by the Spike, the test result will be construed to be "negative" for both antigen and antibody.

PREFERRED EMBODIMENT OF THE INVENTION

In a preferred embodiment of the invention there is provided an assay of a single sample for simultaneous detection of HIV antigen and/or HIV antibody in a human physiological test sample, such as plasma or serum. Microwells, such as of a microtiter plate having microwell strips, are coated with anti-HIV antibody obtained from sera which exhibit high titers of anti-HIV antibody. The solid-phase support media, i.e., the microtiter plate is prepared for the assay by coating the wells with purified anti-HIV antibody derived from a high titer mammalian serum or plasma source such as from a human, goat or other species.

Test sample is added to one coated microwell, or preferably several coated microwells, since duplicate tests are preferred. Control wells are provided for normal, i.e., antigen and antibody negative, physiological fluid, e.g., normal human plasma or serum. An antigen positive control well preferably is also used. A known amount of HIV antigen, i.e. the "Spike" is added to each sample microwell and each control well or wells and the so-combined sample and added antigen subjected to a lyse buffer to assure disruption of virus present in the test sample into its component parts. After a simple incubation at body temperature the microtiter plate is washed to remove material which might interfere with the signal producing system and the captured antigen is next allowed to react with anti-HIV antibody which has been conjugated with biotin. Following a subsequent incubation with streptavidin-peroxidase reagent, color development of bound enzyme is revealed using an appropriate substrate. Resultant optical densities are proportional to the relative amount of HIV antigen, and/or anti-HIV antibody, occurring in the test sample and antigen positive control or the absence thereof in the test sample and controls.

As is customary, the antibody coated solid-phase support and generally all of the reagents necessary for carrying out an assay are provided in kit form. In the practice of the preferred embodiment of this invention such a kit comprises:

A 96 well polystyrene microtiter plate with the wells coated with anti-HIV antibody;
A supply of plate covers;
Lyse Buffer;
Antigen Reagent "Spike";
Antigen Diluent;
Anti-HIV Antibody-Biotin Reagent;
Biotin Reagent Diluent;
Streptaviden-Horseradish Perioxidase (HRPO) Conjugate;
3, 3', 5, 5' Tetramethylbenzidien (TMB) reagent;
TMB Diluent Buffer;
Normal Human Plasma Control;
Normal Human Serum Control;
Antigen Positive Control (50 pg antigen per 20 uL)
10× Wash Buffer;
Hydrogen Peroxide Solution; and
Stopping Solution.

Glossary of Reagents

The reagents are generally required to be prepared in advance so that they will be available at the appropriate steps in carrying out the exemplary preferred immunoassay procedure. These are as follows:

| Lyse Buffer: | |
| --- | --- |
| Peroxide-free octylphenolpoly (ethyleneglycolether) e.g. Triton X-100, Boehringer Mannheim Biochemicals | 5% |
| Polyoxyethylenesorbiton monolaurate e.g. Tween 20, Sigma Chemical Co. | 2% |
| Sodium Ethylmercurithiosalicylate e.g. Thimersol, | |

-continued

Lyse Buffer:

| | |
|---|---|
| Sigma Chemical Co. | 0.05% |
| Dye, FDC Blue No. 1 | 0.9 mg/ml |
| Distilled water | Q.S. 1 L |

Antigen Reagent

HIV antigen content sufficient when diluted with antigen diluent to provide Spike of 50 picograms of HIV antigen per 20 uL of diluted reagent. The concentration of antigen in the Spike may be determined on the basis of P24 equivalent by use of a DuPont P24 Radio-immunoassay (RIA).

| | |
|---|---|
| Antigen Diluent: | |
| Protease-Free Bovine Serum Albumin (BSA) in Phosphate Buffered Saline (PBS) | 1.0% |
| Sodium azide | 0.1% |
| Dye, FDC Red No. 3 | 0.5 mg/ml |
| Anti-HIV Antibody-Biotin Reagent: | |
| Human anti-HIV Antibody-Biotin Conjugate (preferably lyophilized) | |
| Biotin Reagent Diluent: For 1L | |
| Triton X-100 | 0.5% |
| Normal Human Serum (heat inactivated) | 0.5% |
| Tween | 0.2% |
| Thimersol | 0.5% |
| 10X PBS (100 mM phosphate, 1.455 M NaCl pH 7.2) | 100. ml |
| Distilled Water | Q.S. 1 L |
| Streptavidin-HRPO Conjugate: | |
| Calbiochem-Behring Corp. | |
| TMB Reagent: | |
| TMB | 1.0 g |
| DMSO (dimethyl sulfoxide) | Q.S. 100.0 ml |
| TMB Dilution Buffer: | |
| $Na_2HPO_4 \cdot 7H_2O$ | 24.13 g |
| Citric acid monohydrate | 11.38 g |
| Chloracetamide | 1.00 g |
| Distilled water | Q.S. 1 L |
| pH adjusted to 4.4 | |
| Stopping Solution: | |
| 18 M concentrated $H_2SO_4$ | 100.0 ml |
| Distilled water | 800.00 ml |
| Hydrogen Peroxide Solution: | |
| 30% $H_2O_2$ | |
| 10X Wash Buffer (Dilute 1 to 10): | |
| Tween 20 | 10.0 ml |
| 10X PBS | 0.99 L |
| 1% Chloracetamide | 10.0 g |

Depending upon the nature of the reagents, as well as the protocol, it will be appreciated by those skilled in the immunoassay art that the concentration of individual reagents can be varied widely once it is appreciated that a significant aspect of this invention resides in the step of adding a Spike consisting of a known amount of antigen of the single binding pair being assayed.

IMMUNOASSAY PROCEDURE

The immunoassay embodying the invention preferably is performed in a familiar microtiter plate well. In the preferred embodiment, a 200 microliter (uL) patient sample is tested. The patient sample may comprise human plasma derived from whole blood from which the cells have been removed by centrifugation, serum, or cultured cells. The test sample of 200 uL is introduced into the well of the microtiter plate which has been coated with a heat inactivated purified anti-HIV antibody.

The purified anti-HIV antibody is derived from a high titer serum or plasma source. Such a source can be a human one. To coat a well, the mammalian antibody, e.g., human anti-HIV antibody is diluted to 2.5 micrograms per mililiter in so-called "plating buffer". The plating buffer is comprised of 250 mM of potassium phosphate at pH 6.0. 250 uL of diluted antibody is pipetted into the well and stored at 4° C. for approximately sixteen hours. The well is then drained and washed three times in a phosphate buffered saline (PBS) wash solution. The well is then blocked for one hour at room temperature with 325 uL of a blocking reagent comprising 1% bovine serum albumin (BSA) (Protease free), 5% Sucrose plus 1% sodium ethylmercurithiosalicylate in PBS filtered through a 0.2 um filter. The well is then drained, speed vacuum dried and stored at 4° C. in a bag with a desicant bag.

Although the coating procedure has been described for a single well, conventional microtiter plates are available with a plurality of wells. Also available is equipment for coating a plurality of wells. Thus, the immunoassay embodying the invention can be performed utilizing such available equipment with a plurality of wells.

To the 200 uL test sample in the well is added 20 uL of Lyse Buffer for lysing membrane fragments and 20 uL of Human Antigen Working Solution which is the antigen reagent diluted with antigen diluent to the preselected 50 pg antigen per 20 uL. The well is then covered and mixing of ingredients in a suitable shaker is performed for one minute. The mixed materials are then incubated for one hour at 37° C.

After incubation, the well is aspirated and washed three times in a conventional manner with wash buffer. The anti-HIV antibody-biotin which is preferably in a lyophilized state is reconstituted and diluted to a 5% solution with biotin reagent diluent and 200 uL added to the well and the plate incubated at 37° C. for one hour.

After incubation, the well is aspirated and washed three times using the Wash Buffer reagent. Then 200 uL of the streptavidin-peroxidase conjugate is added to the well, covered and incubated for thirty minutes at 37° C. After incubation, the well is aspirated and washed three times with the Wash Buffer. Then, 200 uL of TMB Substrate Solution is introduced to the well, covered and incubated for thirty minutes at room temperature.

Then, 50 uL of 2 Molar sulfuric acid is added to the well to stop the reaction. The optical density of the solution in the well is then read on a microtiter plate reader at a wavelength of 450 nanometers using 570 nanometers as a reference where dual wavelength capability is available. If dual wavelength capability is not utilized, the plate can be read at both wavelengths and the 450 nanometer readings corrected by subtracting the 570 nanometer readings.

The immunoassay embodying the invention provides for a quantitated patient sample including a predetermined quantity of a Spike of inactivated HIV viral antigen, which is detectable at a designated picogram sensitivity, to be introduced into an antibody coated microtiter well. Various conventional incubations follow, using prescribed human developing agents, such as, biotin covalently coupled to a mammalian specie derived anti-HIV antibody such as derived from a human. The coupling is followed by a step of forming a biotin-avidin conjugated peroxidase complex after which the TMB substrate is added to provide colormetric visualization of the reaction. A particularly favorable degree of sensitivity for the test was noted when the anti-HIV antibody biotin conjugate employed a long chain biotin. The concentration of Spike antigen and the antigen in the patient sample placed in the well which binds to the capture antibody coated walls of the well is then recognized by the anti-HIV antibody which is biotinylated and the complex then reacted with the avidin peroxidase and TMB substrate for visualization of the reaction. After stopping the reaction, the EIA readings can be taken to compare against control directed readings.

The reading obtained from the patient test sample is compared to the control readings such as those obtained from normal human plasma free of HIV antigen, anti-HIV antibody, or non-infectious virus subjected to the immunoassay procedure. We have established the reference point for a test result using a patient sample as an increase or decrease of about 30%. Thus, if an optical reading decreases more than 30% from the OD of the Spike, the determination is antibody positive. If the reading increases more than about 30%, the determination is antigen positive.

While an ELISA using a combination of a ligand and receptor, i.e., biotin-avidin protocol for providing a detectable signal for the immunological reactions has been described in the preferred methodology, it will be appreciated that numerous other methodologies may be employed for visualizing the resultant immunological reactions. In this regard, other labels or markers may be employed for visualizing the resultant immunological reactions, such as radionuclides, other enzymes, fluorescers, chemiluminescers, enzyme substrates, particles, e.g., magnetic particles, combinations of ligands and receptors other than biotin and avidin.

A series of tests were conducted in accordance with the above described improved ELISA protocol for simultaneous determination in a single test well of both HIV antigen and/or anti-HIV antibody. The tests were conducted on plasma and serum derived from blood samples obtained at five medical institutes from patients suspected of being exposed to HIV, diagnosed as having an ARC or suspected of having, or diagnosed as having AIDS. In the test series, three 96 well microtiter plates were used to perform 99 assays.

With respect to microtiter plate 1, there were 32 tests run and the 50 pg per 20 ul spike used to establish the base line optical density exhibited an optical density (OD) that equals $0.894 \pm 0.061$. Using an arbitrary guideline of 30% deviation in optical density below and above 0.894, it was established for purposes of the assay that OD of <0.626 equals anti-HIV antibody positive and OD of >1.16 equals HIV antigen positive.

Similarly with respect to plate 2, 34 tests were run and the 50 pg Spike had an OD of $0.715 \pm 0.56$ an OD reading of <0.500 was considered to be anti-HIV antibody positive and OD of >0.93 was considered to be HIV antigen positive.

By the same rationale, with respect to plate 3, 33 tests were run and the 50 pg Spike had an OD of $0.655 \pm 0.59$ whereby an OD of <0.459 was considered to be anti-HIV antibody positive an OD of >0.852 was considered to be HIV antigen positive.

The samples were all subjected to a screening test by an ELISA technique other than that of the present invention and were also subjected to a confirmation test using a Western blot technique for analysis and identification of HIV proteins P24 and GP120 before assigning a "score" of positive or negative to the sample. Of the 99 samples, 70 or 70.7% were determined to be positive to either HIV antigen or anti-HIV antibody and 29 or 29.3% determined to be negative to either HIV antigen or anti-HIV antibody. Of the 70 samples found to be positive, 6 samples or about 6.1% were found to be both HIV antigen and anti-HIV antibody positive. However, the particular significance of the immunoassay comprising the present invention will be appreciated from the fact that 17 of the samples determined to be "positive" were found to only be positive with respect to HIV antigen.

It is a significant advance in immunoassay to have the ability to simultaneously screen a physiological fluid sample in a single test vessel for both antigen and antibody of a single binding pair. In the preferred embodiment of the invention, this enables simultaneous screening, by use of a single test well, a test sample of plasma or serum from donated blood for both anti-HIV antibody and HIV antigen or more importantly the presence of only HIV antigen. The critical need to identify donated blood containing only HIV antigen during that period of time between a person being infected with HIV and when antibodies to the HIV are raised or raised to a sufficient level to be detected by a screening test, need hardly be emphasized.

The test data compiled as a result of the Western blot confirmation tests performed appear to indicate that about 10% of the tests performed by the method of the present invention are subject to a false positive result and about 15% are subject to a false negative determination. It will be appreciated that the percentage of false results may be attributable to factors which were not determined, such as human error in conducting the test or reading the result. Thus, the percentage of apparent false results is not a true reflection of the efficacy of the exemplary test run described herein.

What is claimed is:

1. A single immunoassay for simultaneous detection of antigen and antibody of a single binding pair in a human physiological fluid test sample containing cells and which sample may have circulating antigen, said assay comprising:
   (a) introducing into contact in a single step with a solid surface to which is bound a known quantity of an antibody capable of linking with a corresponding antigenic determinant comprising the other member of said single binding pair, a predetermined volume of said test sample and a predetermined quantity of said antigen selected within a range quantitatively related to the test sample volume selected so as to provide a useful detective signal at a designated picogram concentration when introduced into the test sample volume for a normally negative test sample;
   (b) incubating said test sample and said predetermined quantity of antigen in contact with said surface to form resultant antigen-antibody complexes;
   (c) washing the incubated test sample; and
   (d) incubating the resultant complexes and subjecting same to a labelled antibody conjugate which is capable of linking to said antigenic determinant and which also is capable of yielding a quantitatively measurable signal correlated to the signal for a normal negative test sample to indicate either antigen positive by a signal higher than the signal of said predetermined quantity of antigen, antibody positive by a signal lower than the signal of said predetermined quantity of antigen, or said normal negative for the test sample.

2. The immunoassay of claim 1 and including the step of introducing to the test sample and said predetermined quantity of said antigen of step (a) of a lysing reagent for uniformly releasing antigens available from said cells during incubation.

3. The immunoassay of claim 1 wherein the antigen is HIV antigen and the antibody is anti-HIV antibody.

4. The immunoassay of claim 1 wherein the antibody bound to the solid surface of step (a) which is capable of linking with a corresponding antigenic determinant is derived from mammals selected from the group consisting of humans and goats.

5. The immunoassay of claim 1 wherein the labelled antibody of step (d) is an enzyme labelled antibody.

6. A single enzyme-linked immunosorbent assay wherein the antigen and antibody of a single binding pair in a test sample containing cells and which sample may have circulating antigen is detected, said assay comprising:
   (a) introducing into contact in a single step with a solid surface to which is bound a known quantity of said antibody capable of linking with a corresponding antigenic determinant comprising the other member of said single binding pair, a predetermined volume of said test sample and a predetermined quantity of said antigen selected to provide a useful detectable photometric signal at a designated picogram concentration when introduced into the test sample volume for releasing antigen which may be present in the test sample;
   (b) incubating said test sample and said predetermined quantity of antigen in contact with said surface to form resultant antigen-antibody complexes;
   (c) washing the incubated sample; and
   (d) incubating the resultant complexes and subjecting same to a labelled antibody conjugate which is capable of linking to said antigenic determinant and a substrate suitable for the detection of the resultant complexes which after incubation results in a color detectable signal correlated to the said detectable signal for a normal negative for the test sample.

7. The immunoassay of claim 6 wherein the antigen is HIV antigen and the antibody is anti-HIV antibody.

8. The immunoassay of claim 6 wherein the antibody bound to the solid surface of step (a) which is capable of linking with a corresponding antigenic determinant is derived from mammals selected from the group consisting of humans and goats.

9. The immunoassay of claim 6 wherein the labelled antibody of step (d) is an enzyme labelled antibody.

10. In an enzyme-linked immunosorbent assay for the detection of an antigen and antibody of a single binding pair in a test sample by spectrophotometric measurement, wherein in a single step the test sample is incubated in the presence of and in contact with one member of the single binding pair bound to a solid support, and an enzyme labelled antibody; the improvement comprising:
    introducing to the test sample prior to said incubation of the test sample a predetermined quantity of said antigen of the single binding pair selected to provide a useful detectable photometric signal for a normally negative test sample so that upon completion of the assay there is provided a detectable color signal.

11. The immunoassay of claim 10 wherein the antigen is HIV antigen and the antibody is anti-HIV antibody.

12. The immunoassay of claim 10 wherein the antibody bound to the solid phase of step (a) which is capable of linking with a corresponding antigenic determinant is derived from mammals selected from the group consisting of humans and goats.

13. The immunoassay of claim 10 wherein the enzyme labeled antibody is labelled with an enzyme which provides the said signal.

14. A kit for use in performing an immunoassay according to claim 1 comprising in combination:
    (a) a solid surface to which is bound a know quantity of an antibody capable of linking with a corresponding antigenic determinant comprising the other member of said single binding pair;
    (b) a predetermined quantity of antigen of a known concentration, which antigen comprises the other member of said single binding pair;
    (c) an amount of a lysing agent for uniformly dispensing antigens of said binding pair which may be present in a test sample;
    (d) enzyme labeled antibody;
    (e) a labelled enzyme for coupling to said enzyme labeled antibody; and
    (f) biologically suitable washing, incubating and purifying reagents necessary for visualizing immunological reactions resulting from use of the kit in performing the immunoassay.

* * * * *

UNITED STATES PATENT AND TRADEMARK OFFICE
CERTIFICATE OF CORRECTION

PATENT NO. : 4,870,003
DATED : September 26, 1989
INVENTOR(S) : Kenneth H. Kortright, et al.

It is certified that error appears in the above-identified patent and that said Letters Patent is hereby corrected as shown below:

Column 9,

Claim 6, line 32, after "volume for" insert --a normally negative test sample, and a lysing agent for--;

line 44, after "test sample" insert --to indicate either antigen positive by a signal lower than the signal of said predetermined quantity of antigen, antibody positive by a signal higher than the normal for said predetermined quantity of antigen, or said normal negative for the test sample--.

Signed and Sealed this
Tenth Day of July, 1990

Attest:

HARRY F. MANBECK, JR.

*Attesting Officer*     *Commissioner of Patents and Trademarks*